(12) United States Patent
Carmody

(10) Patent No.: US 10,485,915 B2
(45) Date of Patent: Nov. 26, 2019

(54) COAXIAL DOUBLE FILTER WITH INTEGRATED FILTER SUPPORT

(75) Inventor: Colm M. Carmody, Kerry, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 1104 days.

(21) Appl. No.: 13/994,041

(22) PCT Filed: Dec. 13, 2011

(86) PCT No.: PCT/US2011/064682
§ 371 (c)(1),
(2), (4) Date: Jun. 13, 2013

(87) PCT Pub. No.: WO2012/082761
PCT Pub. Date: Jun. 21, 2012

(65) Prior Publication Data
US 2013/0256241 A1    Oct. 3, 2013

Related U.S. Application Data

(60) Provisional application No. 61/422,932, filed on Dec. 14, 2010.

(51) Int. Cl.
*A61M 1/36* (2006.01)
*B01D 29/11* (2006.01)
*B01D 29/54* (2006.01)
*B29C 45/14* (2006.01)

(52) U.S. Cl.
CPC ............. *A61M 1/36* (2013.01); *B01D 29/114* (2013.01); *B01D 29/117* (2013.01); *B01D 29/54* (2013.01); *B29C 45/14* (2013.01); *A61M 1/3627* (2013.01); *B01D 2201/291* (2013.01); *B01D 2201/298* (2013.01); *B01D 2201/4084* (2013.01); *Y10T 29/4998* (2015.01)

(58) Field of Classification Search
None
See application file for complete search history.

(56) References Cited

U.S. PATENT DOCUMENTS 4,130,622 A * 12/1978 Pawlak ................. B01D 29/111
                                                              264/255
4,303,530 A    12/1981 Shah et al.
4,954,251 A *  9/1990 Barnes .................. B01D 29/23
                                                              210/323.2
(Continued)

FOREIGN PATENT DOCUMENTS

DE        8707478 U1    7/1987
EP        1769835 A2    8/2006
(Continued)

OTHER PUBLICATIONS

ISR for PCT/US2011/064682 dated Jun. 6, 2012.

*Primary Examiner* — Jason M Greene
*Assistant Examiner* — Brad Gordon
(74) *Attorney, Agent, or Firm* — Pauley Erickson & Kottis

(57) ABSTRACT

A filter for blood or the like provides for concentric filtration tubes of flexible permeable filtration material held concentrically for flow in parallel through the filtration material of the filtration tubes. Manufacture of the filter may in-mold support rings and pillars to flexible filtration media, the lowermost support rings which may then be assembled together and fit into a filter housing.

10 Claims, 4 Drawing Sheets

(56) References Cited

U.S. PATENT DOCUMENTS

| | | | | |
|---|---|---|---|---|
| 5,152,890 A | * | 10/1992 | Linnersten | B01D 29/15 210/315 |
| 5,472,537 A | * | 12/1995 | Friel | B01D 29/111 156/308.2 |
| 5,549,821 A | * | 8/1996 | Bounnakhom | B01D 27/06 210/232 |
| 5,860,796 A | * | 1/1999 | Clausen | B01D 29/21 210/416.4 |
| 2002/0170856 A1 | * | 11/2002 | Jaroszczyk | B01D 29/111 210/493.5 |
| 2006/0107638 A1 | * | 5/2006 | Holzmann | B01D 46/0005 55/498 |
| 2008/0190082 A1 | * | 8/2008 | Scott | B01D 46/0005 55/520 |
| 2008/0245719 A1 | * | 10/2008 | Beard | B01D 29/114 210/235 |
| 2009/0065419 A1 | * | 3/2009 | Jiang | B01D 29/21 210/231 |
| 2009/0211959 A1 | * | 8/2009 | Clint | B01D 29/21 210/172.4 |
| 2010/0243554 A1 | | 9/2010 | Herrin et al. | |

FOREIGN PATENT DOCUMENTS

| | | | | |
|---|---|---|---|---|
| GB | 2171024 A | * | 8/1986 | B01D 29/15 |
| WO | 2010111411 A1 | | 9/2010 | |

* cited by examiner

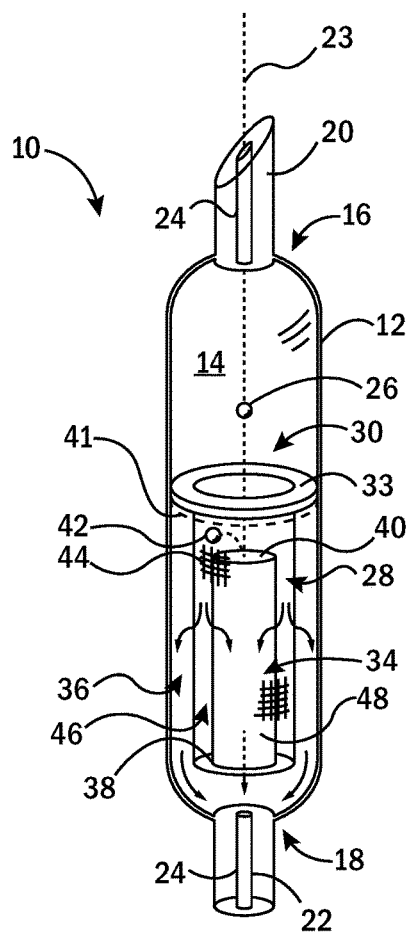
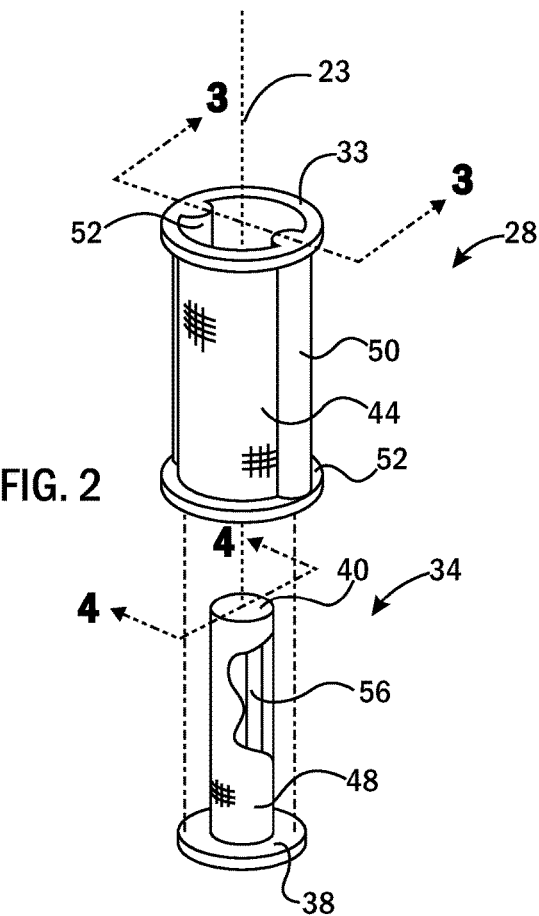
FIG. 1
FIG. 2

COAXIAL DOUBLE FILTER WITH INTEGRATED FILTER SUPPORT

CROSS-REFERENCE TO RELATED APPLICATIONS

The present application is a National Phase of International Application Number PCT/US2011/064982, filed Dec. 13, 2011, and claims the benefit of U.S. application 61/422,932 filed Dec. 14, 2010.

FIELD OF THE INVENTION

The present invention relates to filters and, in particular, to a compact filter suitable for medical applications.

Filters, such as those used for extracorporeal blood filtration in transfusion blood sets, normally provide a housing containing a filter medium formed in a single tube. The filtration medium is designed to remove micro aggregates and clots, as well as non-blood particulate matter.

Often the filter media is a screen type media having a large opening and low thickness to assure low blood velocity at the media interface such as might otherwise produce high shear stresses traumatizing the blood cells. It is important in such filters that filter area be large to increase filter life and reduce the number of filter changes necessary for blood with a large debris load. On the other hand the filter volume is ideally reduced to minimize the blood hold-up volume (the amount of blood retained by the filter) which would reduce blood recovery as well as storage and shipping costs.

SUMMARY OF THE INVENTION

The present invention provides a compact filter design providing parallel filtration paths through to coaxial tube filters, effectively increasing the filter area and reducing shear stress on the fluid while maintaining a small filter volume. Manufacture of the filter is facilitated by stabilizing filter media with injection molded support rings which also serve to conduct liquid properly through the two filter elements in parallel.

Specifically, the present invention provides a filter having an inner and outer filter portion each constructed of (a) a tubular filter element having upper and lower ends separated along a tube axis;(b) thermoplastic upper and lower supports in-molded to respective upper and lower ends of the tubular filter element supporting the upper and lower ends against deformation inward toward the axis;(c) and at least one thermoplastic pillar extending between the thermoplastic upper and lower supports and in-molded to the tubular filter medium element supporting the upper and lower ends in separation along the axis. The thermoplastic lower support for the inner and outer filter portions join to provide a continuous fluid-blocking wall extending between the lower end of the tubular filter element of the inner filter portion and the lower end of the tubular filter element of the outer filter portion.

It is thus a feature of at least one embodiment of the invention to provide a compact high filtration-area filter with reduced filter holdback possible by using thin filter media supported by thermoplastic structure.

The thermoplastic upper support for the tubular filter element of the inner filter portion may block fluid flow through the upper end of its tubular filter element and the thermoplastic upper support for the tubular filter element of the outer filter portion may be open to allow fluid flow through the upper end of its tubular filter element.

It is thus a feature of at least one embodiment of the invention to provide the necessary channeling for parallel filtration in part from the support elements.

The axial length of the tubular filter element for the inner filter portion may be substantially less than the axial length of the tubular filter element for the outer filter portion.

It is thus a feature of at least one embodiment of the invention to reduce splashing on non-filtration surfaces.

The thermoplastic lower supports for the tubular filter elements of the inner and outer filter portions may include mating connectors allowing mechanical inter-engagement of the thermoplastic lower supports to provide the continuous fluid-blocking wall.

It is thus a feature of at least one embodiment of the invention to provide a design that may be readily fabricated with simple injection molds. The mating connectors allow ready manufacture of the filter from separately molded components.

The mating connectors provide a snap connection of the lower supports for the inner and outer filter portions into the continuous fluid-blocking wall.

It is thus a feature of at least one embodiment of the invention to provide a fast attachment mechanism that may be readily implemented manually or through automatic equipment.

The tubular filter elements may be a flexible planar filter medium formed in a tube having a seam extending along the axis and wherein the thermoplastic pillar is in-molded over the seam.

It is thus a feature of at least one embodiment of the invention to provide a thermoplastic conducting channel that may serve to both simplify the mold design and to prevent leakage at the scene of the filter medium.

The outer filter portion may include two diametrically opposed thermoplastic pillars extending between the thermoplastic upper and lower supports and in-molded to the tubular filter medium elements.

It is thus a feature of at least one embodiment of the invention to allow the thermoplastic conducting channels to provide increased axial rigidity to the outer filter tube.

The filter may further include a housing surrounding the inner and outer filter portions, the housing defining a tubular conduit having an inner wall abutting an outer periphery of the upper thermoplastic support of the outer filter portion blocking fluid flow therebetween and spacing an outer surface of the tubular filter element of the outer filter portion from the inner wall for fluid flow therearound.

It is thus a feature of at least one embodiment of the invention to provide a housing that readily integrates with the filter tubes to provide the desired parallel flow through two sets of filter media.

The housing may include axially opposed end walls attached to reduce diameter coupling elements opposed across an axis of the housing to allow the housing to be inserted in series with fluid flow through tubing with the tubing attached to the coupling elements and wherein an upper coupling element is axially aligned with an axis of the inner filter portion.

It is thus a feature of at least one embodiment of the invention to provide a filter housing suitable for medical applications such as blood filtering.

The filter may include standoffs extending between a lower wall of the housing and the lower thermoplastic support of the tubular filter element of the outer filter portion supporting the lower thermoplastic support of the tubular filter element of the outer filter portion to provide fluid flow around the lower thermoplastic support of the tubular filter element of the outer filter portion out of an opening in lower wall.

It is thus a feature of at least one embodiment of the invention to provide for self alignment in the assembly of the filter components reducing the need for jigs or other tooling.

Other features and advantages of the invention will become apparent to those skilled in the art upon review of the following detailed description, claims and drawings in which like numerals are used to designate like features.

BRIEF DESCRIPTION OF THE FIGURES

FIG. 1 is a perspective view in phantom of the filter design of the present invention showing receipt of liquid into an open end of an outer filter tube for passage outward through the outer filter tube to an exit port or inward through a second inner coaxial filter tube to the exit port;

FIG. 2 is an exploded perspective view of the inner and outer filter tube;

DETAILED DESCRIPTION OF THE PREFERRED EMBODIMENT

Figure 3:
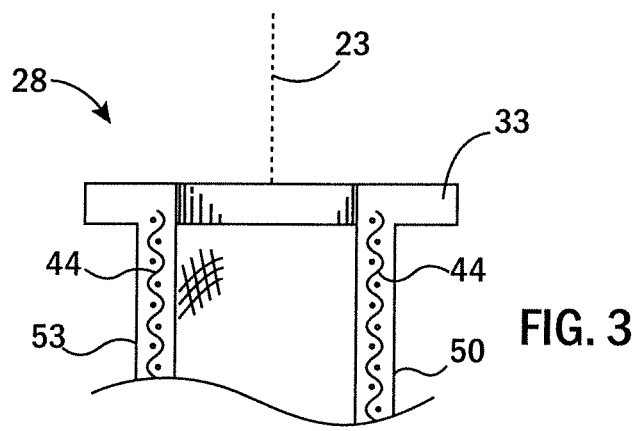
FIG. 3 is a fragmentary cross-section along line 3-3 of FIG. 2 of the outer filter tube showing reinforcing thermoplastic upper support and a support pillar in-molded to the filter media of the outer filter tube.

Referring now to FIG. 1, a filter 10 may provide a housing 12 defining an inner, substantially cylindrical, volume 14 having upper end 16 and lower end 18. Each of the upper end 16 and lower end 18 taper inward to small-diameter couplers 20 and 22 adapted to press fit within standard intravenous tubing for blood transfusions and the like. The couplers 20 and 22 have central lumens 24 aligned with a central axis 23 of the housing 12 and volume 14, each lumen 24 fluidly communicating with the volume 14 so that liquid 26 such as blood may flow in through the upper coupler 20 through the volume 14 to the lower coupler 22.

The volume 14 of the housing 12 holds a filter comprised of a generally tubular outer filter portion 28 fitting coaxially within the volume 14 and coaxially surrounding a generally tubular inner filter portion 34. The outer filter portion 28 has an open upper end 30 that may receive the liquid 26 from the coupler 20 flowing downward under the force of gravity. The outer filter portion 28 includes a thermoplastic support ring 33 that attaches around the opening at the upper end 30 of the outer filter portion 28. The thermoplastic support ring 33 extends radially outward around axis 23 to abut the inner wall of the housing 12 generally preventing downward fluid flow around the outside of the outer filter portion 28 and suspending the outer filter portion 28 away from the inner walls of the housing 12 providing a surrounding passage 36 between the filter medium of the outer filter portion 28 and the inner walls of the housing 12 as will be described.

The inner filter portion 34 is located coaxially within the outer filter portion 28 extending upward from a stop wall 38 at the bottom of the inner filter portion 34, the stop wall 38 spanning a space between lower ends of the outer filter portion 28 and inner filter portion 34. A volume within the inner filter portion 34 opens downward through a central bore in the stop wall 38 and is closed at its upper end by a cap 40, the latter preventing flow of liquid 26 through the upper end of the inner filter portion 34. The height of the inner filter portion 34 is such that the cap 40 is recessed below the support ring 33. As so positioned, liquid 26 striking the cap 40, when splashing upward as indicated by drop 42, is contained within the outer filter portion 28 to be received by a large-diameter tubular filter medium 44 of the outer filter portion 28.

Generally, the diameter of the inner filter portion 34 is smaller than the diameter of the outer filter portion 28 providing a coaxial passage 46 therebetween. Liquid 26 entering the outer filter portion 28 may enter this passage 46 and pass either outward through the large-diameter tubular filter medium 44 of the outer filter portion 28 along the passage 36 and downward to coupler 22, or inward through small-diameter tubular filter medium 48 of the inner filter portion 34 and out the open bottom end of the inner filter portion 34 to coupler 22. These two paths of liquid flow provide for parallel filtration effectively increasing the filtration area of the filter 10.

Referring now to FIGS. 2 and 3, as noted, the outer filter portion 28 includes a large-diameter tubular filter medium 44 such as may be formed by rolling a flexible filter sheet into a tube about axis 23, for example, from a sheet of filtration media such as a polyester screen or the like. The large-diameter tubular filter medium 44 may be held in a cylinder by sewing or other attachment process and the resulting seam retained by a first thermoplastic pillar 50 extending parallel to the axis 23 and in-molded to the material of the large-diameter tubular filter medium 44. The thermoplastic pillar 50 may attach at its upper end to the support ring 33, the latter also in-molded to the filter medium at the upper end of the outer filter portion 28.

A lower end of the thermoplastic pillar 50, in turn, may attach to the lower support ring 52 also in-molded to the large-diameter tubular filter medium 44. As will be understood to those of ordinary skill in the art, the in-molding infuses molten thermoplastic around the fibers of the filter medium with or without fusing thereto.

A second thermoplastic pillar 53 may also extend parallel to the axis 23 and at a location diametrically opposed to the seam and the first thermoplastic pillar 50. The support rings 33 and 52 prevent deformation of the large-diameter tubular filter medium 44 inward toward the axis 23 while the pillars 50 and 53 resist collapse of the support rings 33 and 52 together along axis 23 effectively supporting the large-diameter tubular filter medium 44 against collapse along axis 23.

Figure 4:
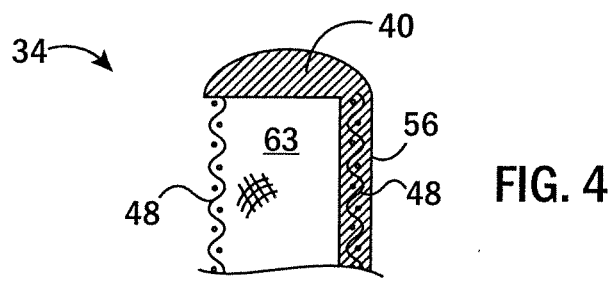
FIG. 4 is a fragmentary cross-sectional view along lines 4-4 of FIG. 2 similar to that of FIG. 3 showing the reinforcing thermoplastic upper support and support pillar in-molded to the filter media of the inner filter tube.

Referring now to FIGS. 2 and 4, the small-diameter tubular filter medium 48 of the inner filter portion 34 may likewise be rolled from a sheet of flexible filtration material and joined by sewing or adhesive at a seam that may be covered by an axially extending support pillar 56 in-molded into the small-diameter tubular filter medium 48 in a manner similar to pillars 50 and 53 of outer filter portion 28. The location of pillar 56 when the inner filter portion 34 is assembled to the outer filter portion 28 may be angularly displaced about axis 23 to lie angularly between pillars 50 and 53.

Pillar 56 joins at its upper end with the cap 40 which may also be in-molded to the upper edge of the small-diameter tubular filter medium 48 to support the small-diameter tubular filter medium 48 in the manner of ring 33 and to block direct flow of liquid 26 into the upper end of the small-diameter tubular filter medium 48 as has been described. A lower end of pillar 56 joins to the stop wall 38 which extends radially outward from the small-diameter tubular filter medium 48 at its lower edge. This stop wall 38 is in-molded to a lower edge of the small-diameter tubular filter medium 48 to serve a similar function as lower support ring 52 in outer filter portion 28. Generally, it will be understood that substantially the entire cylindrical walls of the outer filter portion 28 and inner filter portion 34 are unobstructed, fully exposing the area of the large-diameter tubular filter medium 44 and small-diameter tubular filter medium 48 with the exception of the location of the pillars 50, 53, and 56.

Figure 5:
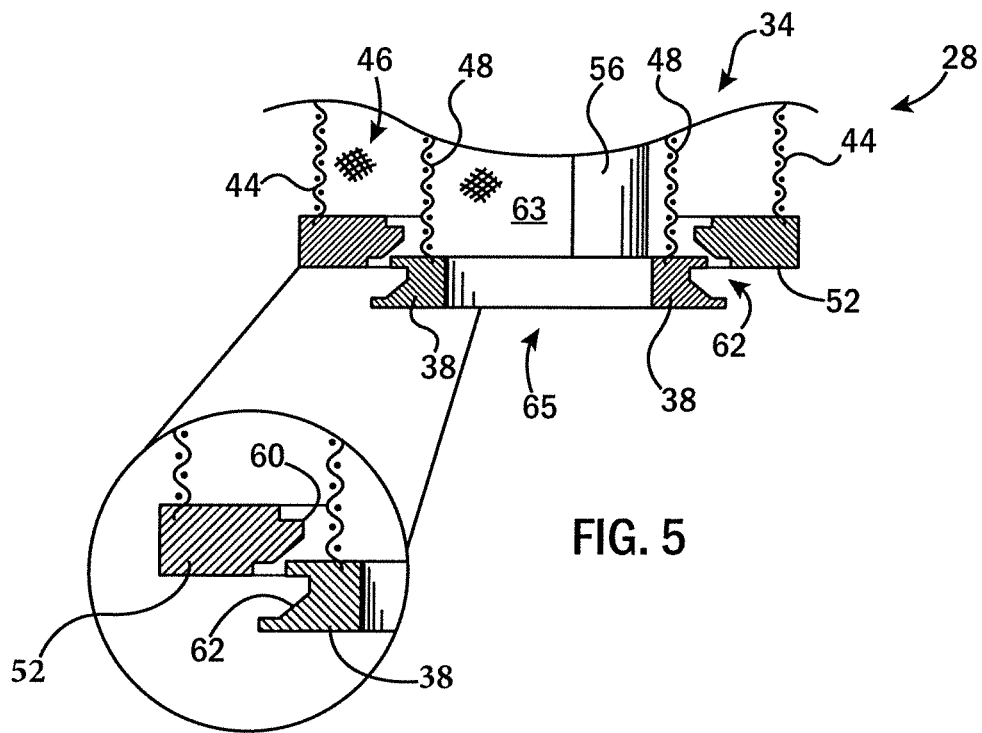
FIG. 5 is a fragmentary cross-sectional view and detail through the assembled inner and outer filter tubes attached together through thermoplastic lower supports by a snap element prior to such snap element.

Referring now to FIG. 5, an inner periphery of the lower support ring 52 of the outer filter portion 28 includes a snap element 60 that may provide a snap engagement with an outer periphery of the stop wall 38 which includes a corresponding snap element 62. The snap elements 60 and 62 which allow joining of the lower support ring 52 and stop wall 38, allow the outer filter portion 28 and inner filter portion 34 to be separately molded and then assembled together by a snap element of the support ring 52 with the stop wall 38.

Figure 6:
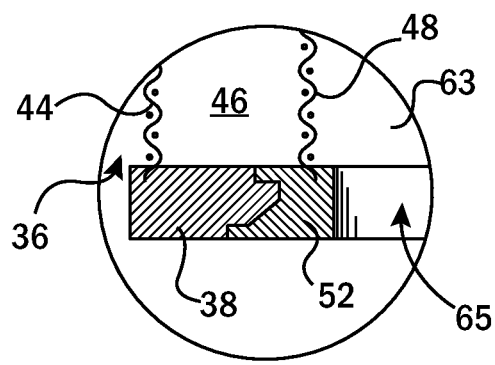
FIG. 6 is a figure similar to the detail view of FIG. 5 showing the thermoplastic lower supports after the snap connection.

As noted above, the stop wall 38 includes a central aperture 65 allowing fluid flowing into the inner filter portion 34 through small-diameter tubular filter medium 48 to be discharged through inner passage 63 within inner filter portion 34 downward out of the inner filter portion 34. As shown in FIG. 6, however, the inner fitting of the stop wall 38 and support ring 52 block fluid flow downward through passage 46, requiring the fluid 26 to pass outward through large-diameter tubular filter medium 44 or inward through small-diameter tubular filter medium 48. The lower edge of the large-diameter tubular filter medium 44, as spaced away from the inner wall of the housing 12, however, does not block fluid flow downward along passage 36 outside of large-diameter tubular filter medium 44. Similarly, the central aperture 65 of the inner filter portion 34 is spaced away from a lower wall of the housing 12 so as not to block fluid flow downward from passage 63 inside small-diameter tubular filter medium 48.

Figure 7:
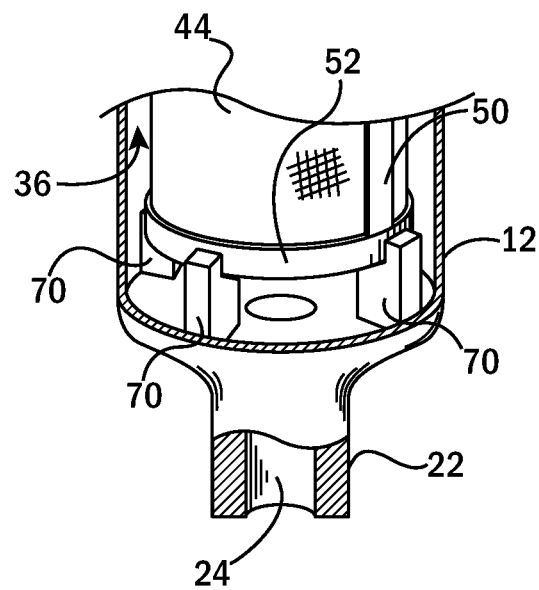
FIG. 7 is a fragmentary cross-sectional view of a lower portion of the filter showing a standoff supporting the outer filter tube above the exit port of the filter.

Referring now to FIG. 7, a lower portion of the housing 12 includes standoffs 70 fitting between an inner wall of the housing 12 and an outer edge of the support ring 52 to center the support ring 52 within the housing 12 and above the bottom wall of the housing 12 to allow free flow of liquid downward in passages 36 around the bottom of the support ring 52 through the lumen 24 of lower coupler 22 as well as out of the passage 63 to the lumen 24.

Figure 8:
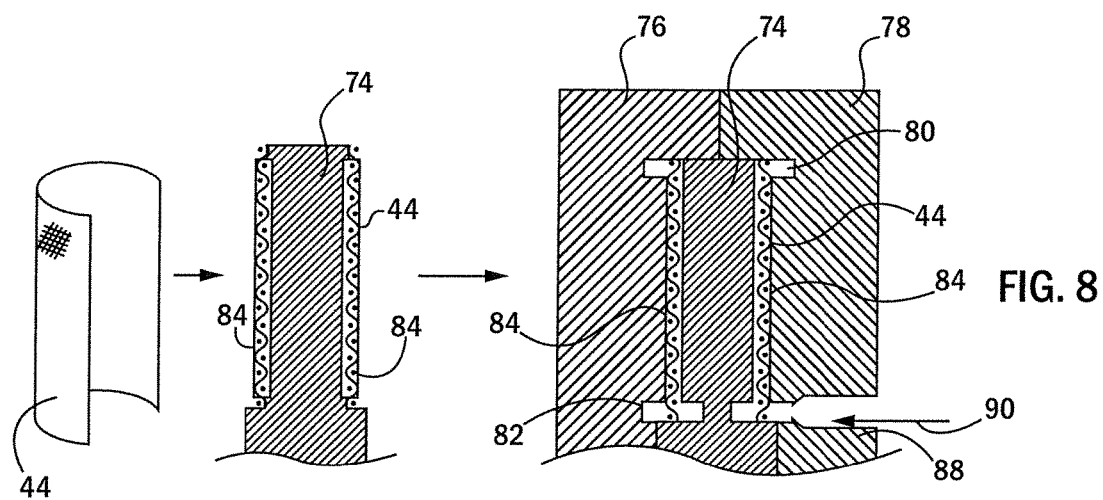
FIG. 8 is a process diagram of a fabrication of the outer filter tube showing an injection mold in cross-section for forming the thermoplastic pillar and upper and lower supports.

Referring now to FIG. 8, manufacture of the filter 10 may include the steps of rolling a planar sheet of filter medium into the tubular form of the large-diameter tubular filter medium 44 and placing the tube on a central mold mandrel 74 being generally a cylindrical plug. Left and right mold portions 76 and 78 may then enclose the mandrel 74 and the large-diameter tubular filter medium 44 to provide mold cavities 80 and 82 corresponding generally to the upper ring 33 and the lower support ring 52 and mold cavities 84 corresponding generally to the pillars 50 and 53. Injected thermoplastic may enter through a port 88 in one of the mold portions 76 and 78 as indicated by arrow 90 to in-mold thermoplastic material into the large-diameter tubular filter medium 44 to the thermoplastic in the location of cavities 84, 80 and 82 to produce the corresponding pillars 50 and 53 and upper ring 33 and lower ring 52. The pillars 50 and 53 provide a conduit for thermoplastic from the port 88 to the upper ring 33. Separation of the mold portions 76 and 78 yield the outer filter portion 28 as shown in FIG. 2 prior to assembly with inner filter portion 34.

Figure 9:
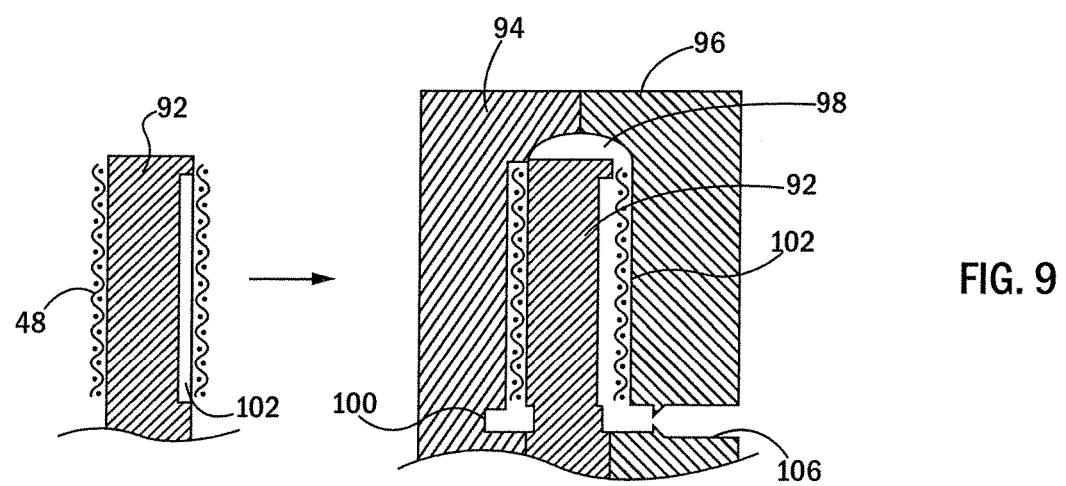
FIG. 9 is a figure similar to that of FIG. 8 showing the molding process for the inner filter tube.

Likewise, as shown in FIG. 9, small-diameter tubular filter medium 48 may be rolled as shown in FIG. 8 and placed around a narrower cylindrical mandrel 92. Again, mold portion 94 and 96 may be placed about the mandrel 92 to define cavities 98 and 100 providing the cap 40 and stop wall 38, and cavity 102 providing the pillar 56. A port 106 allows the injection of molten thermoplastic through mold portion 96 as indicated by arrow 110 into the cavities 100 102 and 98 to form the inner filter portion 34 substantially as shown in FIG. 2. Assembly of the two filter elements may then be completed as indicated in FIG. 5.

It will be appreciated that a more complex molding technique may be used to mold outer filter portion 28 and inner filter portion 34 simultaneously without the need to separately assemble stop wall 38 to support ring 52 at a later manufacturing stage. Rather, the two components may be molded together and joined by a single element stop wall in-molded to both of large-diameter tubular filter medium 44 and small-diameter tubular filter medium 48. It will also be appreciated that snap elements 62 and 60 may be augmented or replaced by adhesive or ultrasonic welding or the like.

The housing 12 may be assembled in halves as separated by a seam 41 (shown in FIG. 1) which may be glued or ultrasonically welded together once the outer filter portion 28 and inner filter portion 34 placed there are supported by the standoffs 70 shown in FIG. 7.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

The invention claimed is:

1. A filter comprising:
    an inner filter portion having a flexible tubular filter element with upper and lower ends separated along a length of the flexible tubular filter element and at least one thermoplastic upper support, and at least one thermoplastic lower support in-molded to the upper and lower ends supporting the upper and lower ends against deformation, and at least one thermoplastic pillar extending between the thermoplastic upper and lower supports and in -molded to the flexible tubular filter element supporting the upper and lower ends in separation;

an outer filter portion surrounding the inner filter portion and having a flexible tubular filter element with upper and lower ends separated along a length of the flexible tubular filter element and at least one thermoplastic upper support, and at least one thermoplastic lower support in -molded to the upper and lower ends supporting the upper and lower ends against deformation, and at least one thermoplastic pillar extending between the thermoplastic upper and lower supports and in-molded to the flexible tubular filter element supporting the upper and lower ends in separation;

a housing surrounding the inner and outer filter portions and having end walls providing an upper coupler and lower coupler respectively on opposite sides of the inner and outer filter portions to receive fluid flow into the housing through the upper coupler to be conducted through at least one of the inner and outer filter portions to exit the housing through the lower coupler;

wherein the thermoplastic lower supports of the inner and outer filter portions join to provide a continuous fluid-blocking wall extending between the lower ends of the inner and outer filter portions, wherein the couplers are adapted to fit within intravenous tubing; and wherein the thermoplastic upper support of the outer filter portion extends outward to contact an inner wall of the housing to guide fluid flow from the upper coupler to a first chamber between the outer filter portion and the inner filter portion so that fluid may flow from the first chamber along two separate paths, a first path passing only through the outer filter portion to a second chamber formed between the outer filter portion and the housing to flow from the second chamber to the lower coupler and a second path passing only through the inner filter portion to a third chamber within the inner filter portion to flow from the third chamber to the lower coupler;

whereby each of the two separate paths of fluid flow may be filtered by a different one of the inner and outer filter portions.

2. The filter of claim 1 wherein the thermoplastic upper support for the flexible tubular filter element of the inner filter portion blocks fluid flow through the upper end of the flexible tubular filter element of the inner filter portion into the inner filter portion and the thermoplastic upper support for the flexible tubular filter element of the outer filter portion is open to allow fluid flow through the upper end of the flexible tubular filter element of the outer filter portion and into the outer filter portion.

3. The filter of claim 1 wherein an axial length of the flexible tubular filter element for the inner filter portion is substantially less than an axial length of the flexible tubular filter element for the outer filter portion.

4. The filter of claim 1 wherein the thermoplastic lower supports for the flexible tubular filter elements of the inner and outer filter portions include mating connectors allowing mechanical inter-engagement of the thermoplastic lower supports to provide the continuous fluid-blocking wall.

5. The filter of claim 4 wherein the mating connectors provide a snap connection of the lower supports for the inner and outer filter portions into the continuous fluid-blocking wall.

6. The filter of claim 1 wherein each of the flexible tubular filter elements comprises a flexible planar filter medium formed in a tube and has a seam and wherein a thermoplastic pillar of the at least one thermoplastic pillar is in-molded over the seam.

7. The filter of claim 1 wherein the outer filter portion includes two diametrically opposed thermoplastic pillars extending between the thermoplastic upper and lower supports of the outer filter portion and in-molded to the flexible tubular filter element of the outer filter portion.

8. The filter of claim 1 further including standoffs extending between a lower wall of the housing and the thermoplastic lower support of the flexible tubular filter element of the outer filter portion, the standoffs supporting the lower thermoplastic support of the flexible tubular filter element of the outer filter portion to provide fluid flow around the lower thermoplastic support of the flexible tubular filter element of the outer filter portion out of an opening in the lower wall.

9. The filter of claim 1 wherein the thermoplastic upper support for the inner filter portion provides a continuous fluid-blocking wall sealing the top of the inner filter portion to block fluid flow from the upper coupler into the third chamber except through sidewalls of the inner filter portion.

10. The filter of claim 1 wherein the thermoplastic upper support for the outer filter portion provides a continuous fluid-blocking wall sealing the top of the outer filter portion to the housing to block fluid flow from the upper coupler into the second chamber except through sidewalls of the outer filter portion.

* * * * *